United States Patent
Yamamura et al.

[11] Patent Number: 5,914,118
[45] Date of Patent: Jun. 22, 1999

[54] MULTI-LAYERED DRUG CONTAINING FILM PREPARATION HAVING POWDER ADHESIVE THEREON

[75] Inventors: Keiko Yamamura; Noboru Tomiya; Manabu Sugimoto; Makoto Usami; Yuji Sato; Yoshiyuki Nagao, all of Nagoya, Japan

[73] Assignee: Sanwa Kagaku Kenkyusho Co., Ltd., Aichi-ken, Japan

[21] Appl. No.: 08/773,632

[22] Filed: Dec. 23, 1996

[30] Foreign Application Priority Data

Dec. 26, 1995 [JP] Japan .................................... 7-338728
Dec. 16, 1996 [JP] Japan .................................... 8-335468

[51] Int. Cl.$^6$ .................................................. A01N 25/34
[52] U.S. Cl. ........................................... 424/402; 424/404
[58] Field of Search ................................... 424/402, 434, 424/447, 449, 404

[56] References Cited

U.S. PATENT DOCUMENTS

Re. 33,093 10/1989 Schiraldi et al. ...................... 424/676
4,713,243 12/1987 Schiraldi et al. ...................... 424/151

FOREIGN PATENT DOCUMENTS

| | | |
|---|---|---|
| 54-41320 | 4/1979 | Japan . |
| 58-128314 | 7/1983 | Japan . |
| 58-213709 | 12/1983 | Japan . |
| 62-56420 | 3/1987 | Japan . |
| 62-135417 | 6/1987 | Japan . |
| 3-246220 | 11/1991 | Japan . |
| 4-266819 | 9/1992 | Japan . |

OTHER PUBLICATIONS

Edited by Masahiro IRIE "Production of Functional Gels of High Molecular Weight Substance and Applications Thereof", p. 77, issused from Kabushiki Kaisha CMC (1987).

*Primary Examiner*—Jose' G. Dees
*Attorney, Agent, or Firm*—Nikaido Marmelstein Murray & Oram LLP

[57] ABSTRACT

A multi-layered film preparation is disclosed having a drug-containing layer which contains at least one water-soluble high molecular weight compound as a main base material, a layer which is made difficult to dissolve in water and positioned at one side of the drug-containing layer and a powdery adhesive compound positioned at the other side of the drug-containing layer.

13 Claims, 3 Drawing Sheets

MULTI-LAYERED DRUG CONTAINING FILM PREPARATION HAVING POWDER ADHESIVE THEREON

BACKGROUND OF THE INVENTION

1. Field of the Invention

The present invention relates to a multi-layered film preparation for pain-killing and protecting an affected part of mucous membrane in the oral cavity and more particularly, to that improved in handling thereof.

2. Related Arts

Hitherto, many proposals have been made on a preparation to be applied on an affected part in mucous membrane, and more particularly to that in oral cavity.

As an adhesive preparation was disclosed in Jap. Pat. No. 54-41320 (A) which comprises a compact mixture or composition to be adhered on mucous membrane in the oral cavity and containing hydroxypropylcellulose, polyacrylic acid or a salt thereof as well as a drug or effective ingredient agent. This preparation has been formed by tabletting granular or powderform ingredients, has thickness of 1 mm or more, and is poor in flexibility. Therefore, such a preparation gives a certain malaise to a patient, when it has been adhered on mucous membrane in the oral cavity, and possibly causes a pain.

For improving such a feeling in use and sustaining power in effect, then, it has been studied on various film preparations having a layer difficult to dissolve in water (non-adhesive layer), as disclosed in Jap. Pat. Nos. 63-18923(B), 58-128314(A), 58-213709(A), 2-60644(B), and 62-56420 (A).

These film preparations solve the feeling in use and sustaining power in effect, but shows such a disadvantage that a force of adhesion becomes low, as a degree of moisture in the area of mucous membrane (affected part) is higher. In order to dissolve the problem, investigations have been made on various adhesive base materials and a combination thereof, as disclosed in Jap. Pat. Nos. 62-135417 (A), 3-33215(B), 6-2669(B), 6-2670(B), 3-246220(A), and 4-266819(A). An amount of the adhesive base material to be composed has also been investigated, but a preparation improved in both of the adhesive force and feeling in use has not yet been developed, since the feeling in use becomes worth due to stickiness, as the amount thereof increases.

A double-layered film preparation consisting of a drug containing layer and non-water soluble layer (non-adhesive layer) has been investigated, since in case of applying an adhesive preparation to an affected part in narrow space as in a oral cavity, the preparation tends to stick to fingers, or slips-off from the affected part. Moreover, triple-layered preparation having an an adhesive layer in addition to said layers, It has also been investigated in order to increase the force of adhesion to mucous membrane in the oral cavity. Such a preparations shows a sufficient force of adhesion, if moisture of the mucous membrane in oral cavity is not so high as in a healthy person, but does not show the sufficient force of adhesion, when an affected part is in highly moist state due to an erosion caused by an infectional disease or side effect through a radiotherapy and/or chemotherapy, so that falling out from the affected part or getting out of its position due to slipping can not be prevented.

SUMMARY OF THE INVENTION

An object of the invention is to provide a multi-layered film preparation which shows excellent adhesion to an affected part of mucous membrane in oral cavity, even if it has been remarkably moisted.

Followings are relations between objects and means for attaining the objects.

Object:

To improve handling of the preparation for preventing adhesion of the preparation to fingers and to prevent slipping of the preparation from the affected part to muscous membrane neighboring thereto.

Means therefor:

To make the preparation as a triple-layered one consisting of an adhesive layer, intermediate layer (a drug containing layer) and layer made difficult to dissolve in water (non-adhesive layer), or as a double-layered one consisting of the adhesive layer (drug containing layer) and the layer made difficult to dissolve in water.

Object:

To keep a sufficient force of adhesion, even if an affected part is remarkably moisted and prevent slipping-off therefrom.

Means therefor:

To select a powder of an adhesive high molecular weight substance for forming the adhesive layer, or disperse such a powder in the drug containing layer. According to this means, adhesiveness of the preparation to mucous membrane can remarkably be improved in comparison with a convention preparation, wherein an adhesive high molecular weight substance is made into a form of film.

Therefore, a multi-layered film preparation according to the invention is characterized by having a drug containing layer which contains a water-soluble high molecular weight substance as a main base material, a non-adhesive layer which is made difficult to dissolve in water and is positioned at one of both surfaces of the drug containing layer, and an adhesive layer positioned to the other surface of the drug containing layer.

Otherwise, a multi-layered film preparation according to the invention is characterized by having a drug containing layer, in which an adhesive high molecular weight substance is dispersed, and a non-adhesive layer which is made difficult to dissolve in water and positioned at one of both surfaces of the drug containing layer.

For increasing the force of adhesion, it is convenient to apply the high molecular weight substance or a gum in the form of powder on the adhesive layer, add the powder into the adhesive layer, or disperse the powder in the adhesive layer, although a conventional film preparation has been formed by dissolving the high molecular weight substance or gum into a solvent, pouring the solution into a mold, and then evaporating the solvent.

As a water-soluble high molecular weight substance to be employed as a main base material for the preparation according to the present invention, following compounds can be listed: water-soluble cellulose derivatives [hydroxypropylcellulose (HPC), hydroxypropylmethylcellulose (HPMC), methylcellulose (MC), carboxymethylcellulose (CMC) and a salt thereof], polyvinyl alcohol, polyethylene oxide and the like, which may be used solely or in a combination thereof. Among them, the hydroxypropylcellulose (HPC) is most preferable, since it is excellent in formability of a softy film.

As an agent for making the layer difficult to dissolve in water, following compounds can be listed: shellac, stearic acid, palmitic acid and the like higher fatty acid; ethylcellulose, cellulose acetate, cellulose butyrate and the like cellulose derivatives having a low solubility to water; hydroxypropyl cellulose phthalate, acetic cellulose phthalate and the like enteric film forming agents. A good layer has been formed in case of using a combination of shellac and HPC, ethylcellulose and HPC as well as using solely the enteric film forming agent.

As an adhesive substance, following compounds can be listed: carboxyvinylpolymer, sodium polyacrylate and the like polyacrylic acid derivatives and its pharmaceutically acceptable non-toxic salts; a copolymer of acrylic acid and its pharmaceutically acceptable non-toxic salts; carboxymethylcellulose, sodium carboxymethylcellulose and the like hydrophilic cellulose derivatives; pullulan, povidone, karaya gum, pectin, xanthane gum, tragacanth, alginic acid, gum arabic, acidic polysaccharide and its derivatives as well as its non-toxic salts. Particularly, carboxyvinylpolymer, sodium polyacrylic acid, pectin and karaya gum were excellent adhesion, when such a substance was applied on the drug containing layer or added therein, in a form of powder.

There is no limitation in preparation of the adhesive layer, if it can keep the state of powder and can be applied on or dispersed in the drug containing layer in a uniform state.

Generally, following methods can be listed for forming the adhesive layer.

(1) By the way for removing a solvent from the drug containing layer, the adhesive high molecular weight substance in the form of powder is applied on the drug containing layer.

(2) The adhesive high molecular weight substance in the form of powder is applied on the drug containing layer, a solution of a water-soluble high molecular substance is sprayed thereon, and then dried.

(3) To the surface of drug containing layer, a suspension of the adhesive high molecular weight substance in a solvent which can dissolve a base material of the drug containing layer, or in a solution of the water-soluble high molecular weight substance is applied, and then dried.

(4) A suspension of the adhesive high molecular weight substance in a solution containing the water-soluble high molecular weight substance and drug is poured on a teflon (trademark) plate, and then a solvent therein is removed.

Various drugs may be applied for the preparation according to the invention such as a local anesthetic agent, analogesical-inflammatoric agent, hemostatic agent, fungicide, antiviral agent, antibiotic, and synthetic antibacterial agent. As the local anesthesias, following compounds can be listed: tetracaine, diethylaminoethyl p-butylaminobenzoate, oxybuprocaine, lidocaine, dibucaine, propytocaine, and salts thereof. As the analogesical-inflammatorical agents, following compounds can be listed: aspirin, acetoaminophen, acemethacine, ibuprofen, indomethacin, ketoprofen, flurbiprofen, glycyrrhizic acid, fulufenamic acid, phenylbutazone, naproxen, oxyhenbutazone, diclofenac sodium, benzydamine, mepirizole, isothipendyl hydrochloride, bufexamac, bendazac, azulene, piroxicam, diflunisal, and the like. As the infalammatorical steroid, following compounds can be listed: triamcinolone acetonide, dexamethazone, hydrocortisone acetate, fluocinolone acetonide, dexamethazone acetate, prednisolone, betametbasone valerate, prednisolone valerate, beclometasone dipropionate, and the like. As the hemostaics, following compounds can be listed: carbazochrome, thrombin, tranexamic acid, and the like. As the fungicides, following compounds can be listed: miconazol, amphotericin B, nystatin, griseofulvin, and the like. As the antiviral agents, following compounds can be listed: aciclovir, vidarabine, and the like. As the antibiotics, following compounds can be listed: penicillin, gentamicin, fladiomicin, cefalexin, phosphomycin, erythromycin, chloramphenicol, tetracycline, and the like. As the synthetic antibacterial agents, following compounds can be listed: ciprofloxacin, fleroxacin, thiamphenicol, and the like. Such a drug can be employed solely or in a combination thereof. By taking a pollution at affected part by bacteria or the like into consideration, can be added into the drug containing layer or adhesive layer a bactericide (iodo, povidone iodo or the like).

For the preparation according to the invention, if necessary, an additive such as a plasticizer, corrective, coloring agent and the like can be added to each layer, in addition to said base material and drug.

As the plasticizer to give softness, following compounds can be listed: polyethyleneglycol ("Macrogol", trademark), propyleneglycol, glycerin, medium chain-length triglyceride (MCT), a copolymer of ethylene oxide and propylene oxide, triacetin, polysorbate, triethyl citrate, lauric acid, sucrose, sorbitol, phthalic acid ester and the like. Among them, it is preferable to use polyethyleneglycol, when hydroxypropylcellulose (PHC) is selected as the water-soluble high molecular weight substance.

As the corrective, following compounds can be listed: citric acid, tartaric acid, fumaric acid and the like organic acids; saccharin, glycyrrhizic acid, sucrose, frucrtose, mannitol and the like sweetening agents; menthol, mentha harb oil and the like refrigerants; a natural and synthetic spices; an edible lake and the coloring agent.

DETAILED DESCRIPTION OF PREFERRED EMBODIMENTS

Figure 1:
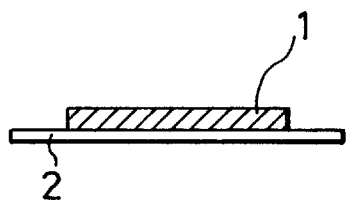
FIG. 1 is a side view showing a first embodiment of a film preparation according to the invention, which has a releasing paper on one of surfaces thereof.
Figure 5:
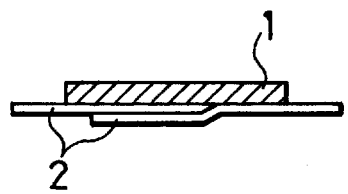
FIG. 5 is a side view showing a third embodiment of a film preparation according to the invention, which has two releasing papers on one surface.
Figure 2:
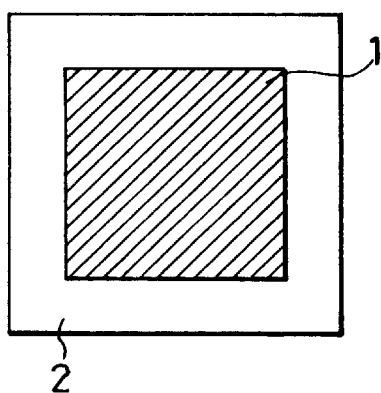
FIG. 2 is a plan view of the first embodiment shown in FIG. 1.
Figure 6:
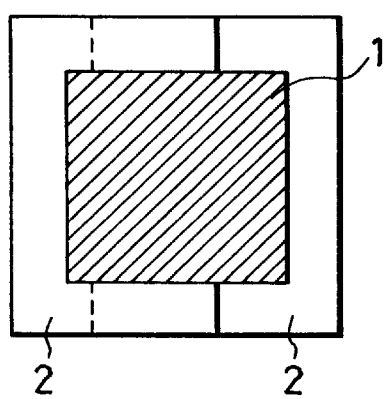
FIG. 6 is a plan view of the third embodiment shown in FIG. 5.
Figure 3:
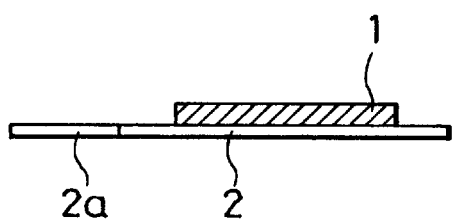
FIG. 3 is a side view showing a second embodiment of a film preparation according to the invention, which has a releasing paper on one of surfaces thereof.
Figure 4:
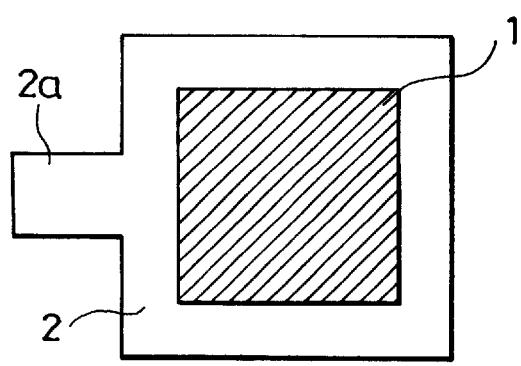
FIG. 4 is a plan view of the second embodiment shown in FIG. 3.

The invention will now be further explained in more detail with reference to Manufacturing Examples, Reference Examples and Test Examples.

EXAMPLE 1

Formation of adhesive layer by powder applying method (1)

A homogeneous solution of hydroxypropylcellulose (1007 mg, viscosity: 150–400 cps as 2% aqueous solution at 20° C.), polyethyleneglycol 400 (20 mg), lidocaine hydrochloride (107 mg) in ethanol (37 ml) was poured into a teflon coated petori dish (diameter: 10 cm) and the solution was gradually dried to obtain a drug containing layer in the dish. Then, a solution of hydroxypropylcellulose (86 mg, viscosity: 150–400 cps as 2% aqueous solution at 20° C.)), polyethyleneglycol 400 (48 mg) and refined shellac (43 mg) in ethanol (6 ml) was sprayed on the drug containing layer, and then dried. The spraying and drying procedures were repeated to obtain a double-layered film preparation in the petri dish. The double-layered film preparation was peeled off from the petori dish and then placed again in the petori dish, so that the drug containing layer directs upward. Carboxyvinyl polymer (190 mg, 100 mesh, containing 0.5% polyacrylic acid, viscosity: 29400–39400 cps as aqueous solution of sodium salt and having pH of 7.0–7.5) was suspended in a solution containing hydroxypropyl cellulose (54 mg, viscosity: 150–400 cps as 2% aqueous solution at 20° C.), polyethyleneglycol 400 (1 mg) and dichloromethane solution (25 ml) to spray the homogeneous suspension on the drug containing layer and dried. The spraying and drying procedures were repeated to obtain a triple-layered film preparation consisting of the adhesive layer, drug containing layer and layer made difficult to dissolve in water.

Comparative Example 1
Formation of adhesive layer by solution applying method (1)

A double-layered film preparation consisting of a drug containing layer and layer made difficult to dissolve in water was prepared as described in Example 1. The film preparation was peeled-off from a teflon coated petori dish, and then turned over and placed again in the petori dish, so that the drug containing layer directs upward. A solution of hydroxypropylcellulose (54 mg, viscosity: 150–400 cps as 2% aqueous at 20° C.), carboxyvinylpolymer (190 mg, polyacrylic acid 0.5%, viscosity: 29400–39400 cps as aqueous solution of pH 7.0–7.5 sodium salt) and polyetyhleneglycol 400 (1 mg) in 50% ethanol solution (50 ml) was splayed on the drug containing layer in the petori dish, and dried. The spraying and drying procedures were repeated to obtain a triple-layered film preparation consisting of the adhesive layer, drug containing layer and layer made difficult to dissolve in water.

EXAMPLE 2
Formation of adhesive layer by powder applying method (2)

A double-layered film preparation consisting of a drug containing layer and layer made difficult to dissolve in water was prepared as described in Example 1. The film preparation was peeled-off from a teflon coated petori dish, and then turned over and placed again in the petori dish, so that the drug containing layer directs upward. A powder of carboxyvinylpolymer (190 mg, 100 mesh, polyacrylic acid 0.5%, viscosity 45000–80000 cps as aqueous solution of sodium salt and having pH of 7.0–7.5) was applied uniformly on the drug containing layer. Further, a solution of hydroxypropylcellulose (54 mg, viscosity: 150–400 cps as 2% aqueous solution at 20° C.) and polyethyleneglycol 400 (1 mg) in ethanol solution (10 ml) was splayed on the surface of carboxyvinylpolymer and dried to obtain a triple-layered film preparation consisting of the adhesive layer, drug containing layer and layer made difficult to dissolve in water.

Comparative Example 2
Formation of adhesive layer by solution applying method (2)

A double-layered film preparation consisting of a drug containing layer and layer made difficult to dissolve in water was prepared as described in Example 2. The film preparation was peeled-off from a teflon coated petori dish, and then turned over and placed again in the petori dish, so that the drug containing layer directs upward. A solution of carboxyvinylpolymer (190 mg, polyacrylic acid 0.5%, viscosity: 45000–80000 cps as aqueous solution of sodium salt and having pH of 7.0–7.5) and polyetyhleneglycol 400 (4 mg) in 50% ethanol solution (50 ml) was splayed on the drug containing layer in the petori dish, and dried. The spraying and drying procedures were repeated to obtain a triple-layered film preparation consisting of the adhesive layer, drug containing layer and layer made difficult to dissolve in water.

EXAMPLE 3
Formation of adhesive layer by powder applying method (3)

A homogeneous solution of hydroxypropylcellulose (503 mg, viscosity: 150–400 cps as 2% aqueous solution at 20° C.), hydroxypropylmethylcellulose 2208 (503 mg, viscosity: 4100–5600 cps as 1% aqueous solution at 20° C.), polyethyleneglycol 400 (30 mg) 30 mg, tetracaine hydrochloride (18 mg) in 50% ethanol solution (56 ml) was poured into a teflon coated petori dish (diameter: 10 cm), and solution was gradually dried to obtain a drug containing layer. A solution of hydroxypropylcellulose (86 mg, viscosity: 150–400 cps as 2% aqueous solution at 20° C.) 86 mg, polyethyleneglycol 400 (48 mg) and stearic acid (43 mg) in 50% ethanol solution was poured into the petori dish and on the drug containing layer for gradually drying the solution to obtain a double-layered film preparation consisting of the drug containing layer and layer made difficult to dissolve in water.

The film preparation was peeled-off from the petori dish, and then turned over and placed again in the petori dish, so that the drug containing layer directs upward. A powder of sodium polyacrylate (190 mg, 100 mesh, viscosity: 200–350 cps as 2% aqueous solution at 20° C. was uniformly suspended in a solution of hydroxypropylcellulose (54 mg, viscosity: 150–400 cps as 2% aqueous solution at 20° C.) and polysolvate 80 (2 mg) in a mixture of ethanol solution and dichloromethane (1:1, 54 mg). The suspension was sprayed on the drug containing layer in the petori dish and dried. The spraying and drying procedures were repeated to obtain a triple-layered film preparation consisting of the adhesive layer, drug containing layer and layer made difficult to dissolve in water.

Comparative Example 3
Formation of adhesive layer by solution applying method (3)

A double-layered film preparation consisting of a drug containing layer and layer made difficult to dissolve in water was prepared as described in Example 3. The film preparation was peeled-off from a teflon coated petori dish, and then turned over and placed again in the petori dish, so that the drug containing layer directs upward. A solution of hydroxypropylcellulose (54 mg, viscosity: 150–400 cps as 2% aqueous solution at 20° C.), sodium polyacrylate (190 mg, viscosity: 200–350 cps as 0.2% aqueous solution at 20° C. and glycerine (25 mg) in 20% ethanol solution (40 ml) was splayed on the drug containing layer in the petori dish and dried. The spraying and drying procedures were repeated to obtain a triple-layered film preparation consisting of the adhesive layer, drug containing layer and layer made difficult to dissolve in water.

EXAMPLE 4
Formation of adhesive layer by powder applying method (4)

A double-layered film preparation consisting of a drug containing layer and layer made difficult to dissolve in water was prepared as described in Example 3. The film preparation was peeled-off from a teflon coated petori dish, and then turned over and placed again in the petori dish, so that the drug containing layer directs upward. The surface of the drug containing layer was moisted and dissolved by spraying ethanol solution, and a powder of sodium polyacrylate (190 mg, 100 mesh, viscosity: 400–600 cps as 0.2% aqueous solution at 20° C. was applied on the surface of the drug containing layer and dried to obtain a double-layered film preparation consisting of the drug containing layer having the adhesive high molecular weight substance powders on outer surface thereof and layer made difficult to dissolve in water.

Comparative Example 4
Formation of adhesive layer by solution applying method (4)

A double-layered film preparation consisting of a drug containing layer and layer made difficult to dissolve in water was prepared as described in Example 4. The film preparation was peeled-off from a teflon coated petori dish, and then turned over and placed again in the petori dish, so that the drug containing layer directs upward. A part of solution of sodium polyacrylate (190 mg, viscosity: 400–600 cps as 0.2% aqueous solution at 20° C.) and D-sorbitol (10 mg) in 20% ethanol solution (40 ml) was poured into the petori dish and on the drug containing layer. The solution in the petori dish was gradually dried. The partial pouring and drying procedures were repeated to obtain a triple-layered film preparation consisting of the adhesive layer, drug containing layer and layer made difficult to dissolve in water.

EXAMPLE 5
Formation of adhesive layer by powder applying method (5)

A homogeneous solution of hydroxypropylcellulose (1007 mg, viscosity 150–400 cps as 2% aqueous solution at 20° C.), polyethyleneglycol 400 (20 mg), dibucaine hydrochloride (9 mg) in ethanol solution (37 ml) was poured into a teflon coated petori dish (diameter: 10 cm), and the solution was gradually dried to obtain a drug containing layer. A solution of hydroxypropylcellulose (86 mg, viscosity: 150–400 cps as 2% aqueous solution at 20° C.), polyethyleneglycol 400 (48 mg) and palmitic acid (43 mg) in ethanol solution (9 ml) was poured into the petori dish and on the drug containing layer, and the solution was gradually dried to obtain a double-layered film preparation consisting of the drug containing layer and layer made difficult to dissolve in water.

The double-layered film preparation was peeled-off from the petori dish, and then turned over and placed again in the petori dish, so that the drug containing layer directs upward. A powder of povidone (190 mg, PVP K90, 100 mesh, viscosity: 300–700 cps as 10% aqueous solution) was applied on the drug containing layer in the petori dish. Then, a solution of hydroxypropylcellulose (40 mg, viscosity: 1000–4000 cps as 2% aqueous solution at 20° C.) and polyethyleneglycol 400 was sprayed on the drug containing layer in the petori dish and dried. The spraying and drying procedures were repeated to obtain a triple-layered film preparation consisting of the adhesive layer, drug containing layer and layer made difficult to dissolve in water.

Comparative Example 5
Formation of adhesive layer by solution applying method (5)

A double-layered film preparation consisting of a drug containing layer and layer made difficult to dissolve in water was prepared as described in Example 3. The film preparation was peeled-off from a teflon coated petori dish, and then turned over and placed again in the petori dish, so that the drug containing layer directs upward. A part of solution of povidone (190 mg, PVP K90, viscosity: 300–700 cps as 10% aqueous solution) and polyethyleneglycol 400 (8 mg) in ethanol solution (40 ml) was poured into the petori dish and on the drug containing layer, and dried. The pouring and drying procedures were repeated to obtain a triple-layered film preparation consisting of the adhesive layer, drug containing layer and layer made difficult to dissolve in water.

EXAMPLE 6
Formation of adhesive layer by powder applying method (6)

Hydroxypropylcellulose (503 mg, viscosity: 1000–4000 cps as 2% aqueous solution 20° C.), hydroxypropylcellulose (503 mg, viscosity: 150–400 cps as 2% aqueous solution at 20° C.), polyethyleneglycol 400 (2 mg) and lidocaine hydrochloride (107 mg) were added into ethanol solution (37 ml) to stir for obtaining a homogeneous solution, and then prulan (190 mg) was added thereto to prepare a suspension. The suspension was poured into a teflon coated petori dish (diameter: 10 cm) and gradually dried the same to obtain a drug containing layer, in which particles of pluran was uniformly dispersed. A part of solution of hydroxypropylmethylcellulose phthalate 220731 (86 mg) and polyethyleneglycol 400 (9 mg) in a mixture of ethanol solution and methylelne chloride (1:1, 9 ml) was sprayed on the surface of the drug containing layer in the petori dish. The spraying and drying procedures were repeated to obtain a double-layered film preparation consisting of the drug containing layer, on which particles of the adhesive high molecular substance appear and layer made difficult to dissolve in water.

Comparative Example 6
Formation of adhesive layer by solution applying method (6)

A homogeneous solution of hydroxypropylcellulose (503 mg, viscosity: 1000–4000 cps as 2% aqueous solution at 20° C.), hydroxypropylcellulose (503 mg, viscosity: 150–400 cps as 2% aqueous solution at 20° C.), polyethyleneglycol 400 (20 mg) and lidocaine hydrochloride (107 mg) in ethanol solution (37 ml) was poured into a teflon coated petori dish (diameter: 10 cm), and the solution was gradually dried to obtain a drug containing layer. A solution of hydroxypropylmethylcellulose phthalate 220731 (86 mg) and polyethyleneglycol 400 (9 mg) in a mixture of ethanol solution and methylene chloride (1:1, 9 ml) was sprayed on the surface of the drug containing layer in the petori dish and dried. The spraying and drying procedures were repeated to obtain a double-layered film preparation consisting of the drug containing layer and layer made difficult to dissolve in water.

The film preparation was peeled-off from the petori dish, and then turned over and placed again in the petori dish, so that the drug containing layer directs upward. A part of solution of pluran (190 mg) and glycerine (19 mg) in water (25 ml) was poured into the petori dish and on the drug containing layer, and dried. The pouring and drying procedures were repeated to obtain a triple-layered film preparation consisting of the adhesive layer, drug containing layer and layer made difficult to dissolve in water.

EXAMPLE 7
Formation of adhesive layer by powder applying method (7)

A homogeneous solution of hydroxypropylcellulose (503 mg, viscosity: 1000–4000 as 2% aqueous solution at 20° C.), methylcellulose (503 mg, viscosity: 7000–10000 cps as 2% aqueous solution at 20° C.), glycerine (20 mg) and dibucaine hydrochloride (9 mg) in 70% ethanol solution (56 ml) was poured into a teflon coated petori dish (diameter: 10 cm), and the solution was gradually dried to obtain a drug containing layer. A part of solution of hydroxypropylcellulose (86 mg, viscosity: 150–400 cps as 2% aqueous solution at 20° C.), polyethyleneglycol 400 (48 mg) and refined shellac (43 mg) in ethanol solution (5.9 ml) was poured into the petori dish and on the drug containing layer and gradually dried to obtain a double-layered film preparation consisting of the drug containing layer and layer made difficult to dissolve in water.

The double-layered film preparation was peeled-off from the petori dish, and then turned over and placed again in the petori dish, so that the drug containing layer directs upward. The outer surface of drug containing layer was moisted by spraying 10% ethanol solution, and then a powder of sodium carboxymethylcellulose (190 mg, 100 mesh, viscosity: 1000–1400 cps as 1% aqueous solution at 25° C.) was applied on the drug containing layer in the petori dish and dried to obtain a double-layered film preparation consisting of the drug containing layer with the adhesive high molecular weight substance powders at its outer surface and layer made difficult to dissolve in water.

Comparative Example 7
Formation of adhesive layer by solution applying method (7)

A double-layered film preparation was prepared as described in Example 7. The film preparation was peeled-off from a teflon coated petori dish, and then turned over and placed again in the petori dish, so that the drug containing layer directs upward. A part of solution of sodium carboxymethylcellulose (190 mg, viscosity: 1000–1400 cps as 1% aqueous solution at 25° C.), glycerine (9 mg) in 10% ethanol solution (40 ml) was poured into the petori dish and on the drug containing layer and dried. The pouring and drying procedures were repeated to obtain a triple-layered film preparation consisting of the adhesive layer, drug containing layer and layer made difficult to dissolve in water.

EXAMPLE 8
Formation of adhesive layer by powder applying method (8)

A homogeneous solution of hydroxypropylcellulose (503 mg, viscosity 1000–4000 cps as 2% aqueous solution at 20° C.), methylcellulose (viscosity of the 2% solution is 7000–10000 cps at 20° C.), glycerine (20 mg) and dibucaine hydrochloride (9 mg) in 70% ethanol solution (56 ml) was poured into a teflon coated petori dish (diameter: 10 cm), and the petori dish was left to stand for. At the time when the content in the petori dish was somewhat dried, a powder of sodium carboxymethylcellulose (190 mg, 100 mesh, viscosity: 6500–8000 cps as 1% aqueous solution at 20° C.) was uniformly sprayed on the content in the petori dish, and then dried on the whole to obtain a drug containing layer with the adhesive high molecular weight substance on one surface thereof.

The drug containing layer was peeled-off from the petori dish, and then turned over and placed again in the petori dish, so that the drug containing layer directs upward. A solution of hydroxypropylcellulose (86 mg, viscosity: 150–400 cps as 2% aqueous solution at 20° C.), polyethyleneglycol 400 (48 mg) and refined shellac (43 mg) in ethanol solution (5.9 ml) was poured into the petori dish, and the solution was gradually dried to obtain a double-layered film preparation consisting of the drug containing layer with the adhesive high molecular weight substance thereon and layer made difficult to dissolve in water.

Comparative Example 8
Formation of adhesive layer by solution applying method (8)

A double-layered film preparation consisting of a drug containing layer and layer made difficult to dissolve in water was prepared as described in Example 7. The film preparation was peeled-off from a teflon coated petori dish, and then turned over and placed again in the petori dish, so that the drug containing layer directs upward. A part of solution of sodium carboxymethylcellulose (190 mg, viscosity: 6500–8000 cps as 1% aqueous solution at 25° C.) and glycerine (20 mg) in 10% ethanol solution (40 ml) was poured into the petori dish and on the drug containing layer and gradually dried. The pouring and drying procedures were repeated to obtain a triple-layered film preparation consisting of the adhesive layer, drug containing layer and layer made difficult to dissolve in water.

EXAMPLE 9
Formation of adhesive layer by powder applying method (9)

A homogeneous solution of hydroxypropylcellulose (1007 mg, viscosity 150–400 as 2% aqueous solution at 20° C.) 503 mg, polyethyleneglycol 400 (20 mg) and dibucaine hydrochloride (9 mg) in ethanol solution (37 ml) was poured into a teflon coated petori dish (diameter: 10 cm), and the solution was gradually dried to obtain a drug containing layer. A part of solution of hydroxypropylcellulose (86 mg, viscosity: 150–400 cps as 2% aqueous solution at 20° C.), polyethyleneglycol 400 (48 mg) and refined shellac (43 mg) in ethanol solution (5.9 ml) was sprayed on the drug containing layer and then dried. The spraying and drying procedures were repeated to obtain a double-layered film preparation consisting of the drug containing layer and layer made difficult to dissolve in water.

The double-layered film preparation was peeled-off from the petori dish, and then turned over and placed again in the petori dish, so that the drug containing layer directs upward. On the outer surface of drug containing layer, pectin (190 mg) was uniformly applied. A solution of hydroxypropylcellulose (40 mg, viscosity: 150–400 cps as 2% aqueous solution at 20° C.) and polyethyleneglycol 400 (0.8 mg) in ethanol solution (15 ml) was sprayed on the pectin layer and dried. The spraying and drying procedures were repeated to obtain a triple-layered film preparation consisting of the adhesive layer, drug containing layer and layer made difficult to dissolve in water.

Comparative Example 9
Formation of adhesive layer by solution applying method (9)

A double-layered film preparation consisting of a drug containing layer and layer made difficult to dissolve in water was prepared as described in Example 9. The film preparation was peeled-off from a teflon coated petori dish, and then turned over and placed again in the petori dish, so that the drug containing layer directs upward. A part of solution of pectin (190 mg), hydroxypropylcellulose (18 mg, viscosity: 150–400 cps as 2% aqueous solution at 20° C.) and polyethyleneglycol 400 (6 mg) in water (50 ml) was sprayed on the drug containing layer in the petori dish, and then dried. The spraying and drying procedures were repeated to obtain a triple-layered film preparation consisting of the adhesive layer, drug containing layer and layer made difficult to dissolve in water.

EXAMPLE 10
Formation of adhesive layer by powder applying method (10)

A homogeneous solution of polyvinylalcohol (partially saponificated substance, 1007 mg, viscosity: 40–50 cps as 4% aqueous solution at 20° C.), glycerin (30 mg) and dibucaine hydrochloride (18 mg) in water (25 ml) was poured into a teflon coated petori dish (diameter: 10 cm) and the solution was gradually dried to obtain a drug containing layer. A suspension was prepared by dissolving hydroxypropylmethylcellulose acetate succinate (86 mg) and triethyl citrate (18 mg) into a mixture of ethanol solution and methylenechloride (1:1, 9 ml), adding thereto titanium oxide (0.4 mg), and then stirring on the whole. A part of the suspension was sprayed on the drug containing layer in the petori dish and dried. The spraying and drying procedures were repeated to obtain a double-layered film preparation consisting of the drug containing layer and layer made difficult to dissolve in water.

The double-layered film preparation was peeled-off from the petori dish, and then turned over and placed again in the petori dish, so that the drug containing layer directs upward. A suspension was prepared by dissolving hydroxypropylcellulose (54 mg, viscosity: 6–10 cps as 2% aqueous solution at 20° C.) and polysolvate 80 (10 mg, trademark) in a mixture of ethanol and dichloromethane (1:1, 20 ml), and uniformly dispersing thereto karaya gum (190 mg) and lake aluminum (Yellow No. 5, 0.4 mg). The suspension was poured into the petori dish and on the drug containing layer and dried to obtain a triple-layered film preparation consisting of the adhesive layer, drug containing layer and layer made difficult to dissolve in water.

Comparative Example 10
Formation of adhesive layer by solution applying method (10)

A double-layered film preparation consisting of a drug containing layer and layer made difficult to dissolve in water was prepared as described in Example 10. The double-layered film preparation was peeled-off from a teflon coated petori dish, and then turned over and placed again in the petori dish, so that the drug containing layer directs upward. A suspension was prepared by dissolving karaya gum (190 mg), hydroxypropylcellulose (18 mg, viscosity: 6–10 cps as 2% aqueous solution at 20° C.) and polyethyleneglycol 400 (6 mg) in 10% ethanol solution (50 ml), and then uniformly dispersing lake aluminum (Yellow No. 5, 0.4 mg). The suspension was poured into the petori dish and on the drug containing layer and dried in vacuo to obtain a triple-layered film preparation consisting of the adhesive layer, drug containing layer and layer made difficult to dissolve in water.

Comparative Example 11
Formation of adhesive layer by solution applying method (11)

A double-layered film preparation consisting of a drug containing layer and layer made difficult to dissolve in water was prepared as described in Example 1. The double-layered film preparation was peeled-off from a teflon coated petori dish, and then turned over and placed again in the petori dish, so that the drug containing layer directs upward. A part of solution of hydroxypropylcellulose (54 mg, viscosity: 150–400 cps as 2% aqueous solution at 20° C.), carboxyvinylpolymer (410 mg, polyacrylic acid: 0.5%, viscosity: 29400–39400 cps as aqueous solution of sodium salt and having pH of pH 7.0–7.5) and polyethylene chloride 400 (10 mg) in 50% ethanol solution (100 ml) was sprayed on the drug containing layer in the petori dish, and then dried. The spraying and drying procedures were repeated to obtain a triple-layered film preparation consisting of the adhesive layer, drug containing layer and layer made difficult to dissolve in water.

Comparative Example 12
Formation of adhesive layer by solution applying method (12)

A double-layered film preparation consisting of a drug containing layer and layer made difficult to dissolve in water was prepared as described in Example 7. The double-layered film preparation was peeled-off from a teflon coated petori dish, and then turned over and placed again in the petori dish, so that the drug containing layer directs upward. A part of solution of sodium carboxymethylcellulose (570 mg, viscosity: 1000–1400 cps as 1% aqueous solution at 25° C.) and glycerine (27 mg) in 10% ethanol solution (40 ml) was poured into the petori dish and on the drug containing layer, and the solution was gradually dried. The spraying and drying procedures were repeated to obtain a triple-layered film preparation consisting of the adhesive layer, drug containing layer and layer made difficult to dissolve in water.

EXAMPLE 11

Formation of adhesive layer by application machine

A homogeneous solution was prepared by dissolving hydroxypropylcellulose (329 mg, viscosity: 150–400 cps as 2% aqueous solution at 20° C.), ethylcellulose (329 mg) and polyethyleneglycol 400 (243 mg) were into ethanol solution (7.2 ml) and the solution was charged into an application machine (Type YBA applicator and manufactured by Baker Instruments Corp.) to develop the same having a size of 20×20 cm$^2$ and thickness of 187 $\mu$m and dried to obtain a layer made difficult to dissolve in water. A solution of hydroxypropylcellulose (5468 mg, viscosity: 150–400 cps as 2% aqueous solution at 20° C.), polyethyleneglycol 400 (109 mg) and dibucaine hydrochloride (100 mg) in ethanol (121 ml) was applied on the said layer in in thickness of 600 $\mu$m and then dried. The procedures of applying the drug containing solution and drying were repeated by 8 times to obtain a double-layered film preparation consisting of the drug containing layer and layer made difficult to dissolve in water.

To ethanol solution (9 ml), hydroxypropylcellulose (268 mg, viscosity: 150–400 cps as 2% solution at 20° C.) and polyethyleneglycol 400 (946 mg), 946 mg were dissolved, and then pectin (946 mg) was uniformly dispersed therein to prepare a suspension. The suspension was applied on the drug containing layer of double-layered film preparation, in thickness of 450 $\mu$m and dried to obtain a triple-layered film preparation consisting of the adhesive layer, drug containing layer and layer made difficult to dissolve in water.

EXAMPLE 12

Manufacture of film preparation containing inflammatoric and analgesic agent

By treating as described in Example 11, excepting that diclofenac sodium (100 mg) was selected in stead of dibucaine hydrochloride to obtain a triple-layered film preparation.

EXAMPLE 13

Manufacture of film preparation containing inflammatoric and analgesic agent

By treating as described in Example 11, excepting that sodium difrunisal (500 mg) was selected in stead of dibucaine hydrochloride to obtain a triple-layered film preparation.

EXAMPLE 14

Manufacture of film preparation containing antiflammatoric steroid

By treating as described in Example 11, excepting that triamcinolone acetonide (5 mg) was selected in stead of dibucaine hydrochloride to obtain a triple-layered film preparation.

EXAMPLE 15
Manufacture of film preparation containing hemostatic

By treating as described in Example 11, excepting that tranexamic acid (100 mg) was selected in stead of dibucaine hydrochloride to obtain a triple-layered film preparation.

EXAMPLE 16
Manufacture of film preparation containing fungicide

By treating as described in Example 11, excepting that amphotericin B (100 mg) was selected in stead of dibucaine hydrochloride to obtain a triple-layered film preparation.

EXAMPLE 17
Manufacture of film preparation containing an fungicide

By treating as described in Example 11, excepting that nystatin (300 mg) was selected in stead of dibucaine hydrochloride to obtain a triple-layered preparation.

EXAMPLE 18
Manufacture of film preparation containing antiviral

By treating as described in Example 11, excepting that vidarabine (300 mg) was selected in stead of dibucaine hydrochloride to obtain a triple-layered preparation.

EXAMPLE 19
Manufacture of film preparation containing antiviral

By treating as described in Example 11, excepting that aciclovir (500 mg) was selected in stead of dibucaine hydrochloride to obtain a triple-layered preparation.

EXAMPLE 20
Manufacture of film preparation containing antibiotic

By treating as described in Example 11, excepting that chloramphenicol (100 mg) was selected in stead of dibucaine hydrochloride to obtain a triple-layered preparation.

EXAMPLE 21
Manufacture of film preparation containing antibiotic

By treating as described in Example 11, excepting that sulfuric fradiomycin (50 mg) was selected in stead of dibucaine hydrochloride to obtain a triple-layered preparation.

EXAMPLE 22
Manufacture of film preparation containing synthetic antibacterial drug By treating as described in Example 11, excepting that thiamphenicol (50 mg) was selected in stead of dibucaine hydrochloride to obtain a triple-layered preparation.

EXAMPLE 23
Manufacture of film preparation containing a mixture of drugs

By treating as described in Example 11, excepting that thimphenicol (50 mg) was added in addition of dibucaine hydrochloride (100 mg) to obtain a triple-layered preparation.

EXAMPLE 24
Manufacture of film preparation containing a mixture of drugs

By treating as described in Example 11, excepting that miconazole nitrate (39 mg), chloramphenicol palmitate (50 mg), dexamethasone (2 mg) and guaiazulene (6 mg) were added in addition of dibucaine hydrochloride (100 mg) to obtain a triple-layered preparation.

Test Example 1

(Evaluation of adhesion)

Each of preparations obtained by Examples and "Waplon P" (exemplar known film preparation, trademark) were selected as Test Preparations and Control Preparation, and a force of adhesion thereof was evaluated. However, the test was carried out under 2 different conditions, since it has been supposed that mucous membrane in the oral cavity was somewhat dry or moist condition. The moist condition was set by gargling with 100 ml of water just before the test.

The evaluation was given by a panel of healthy persons (10 members) based on following standards.

Score The contents of evaluation

1 Enable to apply steadily on mucous membrane in oral cavity and do not come off by movement of mucous membrane (expansion and contraction) after applied thereon and do not move easily by a tongue.

2 Enable to apply steadily on mucous membrane in oral cavity. Do not come off by movement of cheek, but it moves by force of tongue.

3 Enable to come off easily, or cannot be applied on mucous membrane in oral cavity.

Results of the test are shown in following Table 1. As apparently seen therefrom, all of preparations including test and control ones show good force of adhesion, when the mucous membrane is in dry state, but in moist state, the preparations obtained by Examples 1–10 show better result in comparison with the preparations obtained by Comparative Examples 1–10 as well as control preparation. Particularly, excellent adhesion has been obtained, when carboxyvinylpolymer or pectin were used as a base material.

TABLE 1

| Preparations | Base of the adhesive layer (viscosity) | Result of evaluation (ave. of score) wet state | dry state |
|---|---|---|---|
| Example 1 | carboxyvinylpolymer | 1.2 | 1.0 |
| Comp. Ex. 1 | (29400–39400 cps) | 2.4 | 1.0 |
| Example 2 | carboxyvinylpolymer | 1.0 | 1.0 |
| Comp. Ex. 2 | (45000–80000 cps) | 2.1 | 1.0 |
| Example 3 | sodium polyacrylic acid | 2.2 | 1.5 |
| Comp. Ex. 3 | (200–350 cps) | 3.0 | 1.5 |
| Example 4 | sodium polyacrylic acid | 2.1 | 1.2 |
| Comp. Ex. 4 | (400–600 cps) | 3.0 | 1.4 |
| Example 5 | povidone | 1.6 | 1.3 |
| Comp. Ex. 5 | (300–700 cps) | 2.9 | 1.6 |
| Example 6 | pullulan | 1.5 | 1.4 |
| Comp. Ex. 6 | (300–700 cps) | 3.0 | 1.2 |
| Example 7 | sodium carboxymethyl- | 1.6 | 1.2 |
| Comp. Ex. 7 | cellulose (1000–1400 cps) | 2.7 | 1.5 |
| Example 8 | sodium carboxymethyl- | 1.5 | 1.2 |
| Comp. Ex. 8 | cellulose (6500–8000 cps) | 2.8 | 1.4 |
| Example 9 | pectin | 1.2 | 1.3 |
| Comp. Ex. 9 | | 3.0 | 1.2 |
| Example 10 | karaya gum | 1.4 | 1.3 |
| Comp. Ex. 10 | | 2.8 | 1.4 |
| Waplon P | | 3.0 | 1.1 |

In the table,

Example: powder applying method,

Comp. Ex.: solution applying method.

Test Example 2

(Evaluation on feeling in use)

Feeling in use was checked between preparations obtained by Example 1 and Comparative Example 11 as well as Examples 7 and Comparative Example 12 by a panel of 5 healthy persons. In connection with this, it had previously been confirmed that the force of adhesion of the preparations obtained by Examples 1 and Comparative Example 11 as well as Example 7 and Comparative Example 12 are substantially same, respectively, in case of those shall be applied on mucous membrane in oral cavity, in moist state.

Results are shown in following Table 2. It suggests that the preparations obtained by Comparative Examples gives highly sticky feeling and are not preferable than those obtained by Examples. In other words, such a fact has been confirmed that a preparation, in which an amount of added adhesive material is lesser, gives better feeling in use, if preparations have same force of adhesion.

TABLE 2

| feeling in use after lapsed 1 hour | Number of panelist | | | |
|---|---|---|---|---|
| | Ex. 1 | Comp. Ex. 11 | Ex. 7 | Comp. Ex. 12 |
| No problem | 0 | 0 | 0 | 0 |
| There is sticky feeling in applied part, but can bear | 5 | 1 | 4 | 1 |
| There is sticky feeling in applied part, feel displeasure | 0 | 3 | 1 | 4 |
| There is sticky feeling in applied part, but cannot bear | 0 | 1 | 0 | 0 |

Test Example 3

(Identification of adhesive layer and non-adhesive layer)

An identification test on adhesive layer and non-adhesive layer have been carried out with use of preparations obtained by Examples 1 and 10, Comparative Examples 1 and 10 as well as "Waplon P" (exemplar known film preparation, trademark) and by a panel of 10 persons of 60 years old or more. The test was carried out by 3 times to each sample preparation to avoid a possible misjudgement.

Each of the preparations obtained by Example 10 and Comparative Example 10 as well as Waplon P has been colored to make easy identification of its adhesive layer by eyesight. While, the preparations obtained by Examples 1 and 10 have been manufactured by the powder application method and thus there is given a possibility for identifying the adhesive layer by a tactile sense.

Results are shown in following Table 3. It is apparent therefrom that the preparations obtained by Examples 1 and 10 are excellent.

TABLE 3

| Preparation | Coloring | Number of distinguished persons among 10 panelists | |
|---|---|---|---|
| | | Perfect | Less than 2 times |
| Example 1 | No | 8 | 2 |
| Example 10 | Yes | 9 | 1 |
| Comp. Ex. 1 | No | 1 | 9 |
| Comp. Ex. 10 | Yes | 4 | 6 |
| Waplon P | Yes | 5 | 5 |

Test Example 4

(Evaluation on feeling in taking out from packed preparation)

The preparation obtained by Example 2 had been into pieces 1 having a square form and a releasing paper 2 was adhered on the adhesive layer of each piece, in various manner as shown in FIGS. 1–6 and packed in a package of aluminum foil to make Test Preparations A–C. The Test Preparations A, B and C are shown in FIGS. 1 and 2, 3 and 4 as well as 5 and 6, respectively.

The test was carried out with use of the Test Preparations A–C and Waplon P as a control and by 10 old persons having 60 years or more evaluation thereof had been given under following standards.

Score 1: Easy to peel off the releasing paper from the preparation,

Score 2: Difficult to peel off the releasing paper from the preparation,

Score 3: Very difficult to peel off the releasing paper from the preparation, and Score 4: Impossible to peel off the releasing paper from the preparation.

Results are in following Table 4.

TABLE 4

| Preparation Test Preparation | Average of Score |
|---|---|
| A | 3.8 |
| B | 2.2 |
| C | 1.6 |
| Waplon P | 2.9 |

Test Example 5

(Evaluation on force of adhesion)

Figure 7:
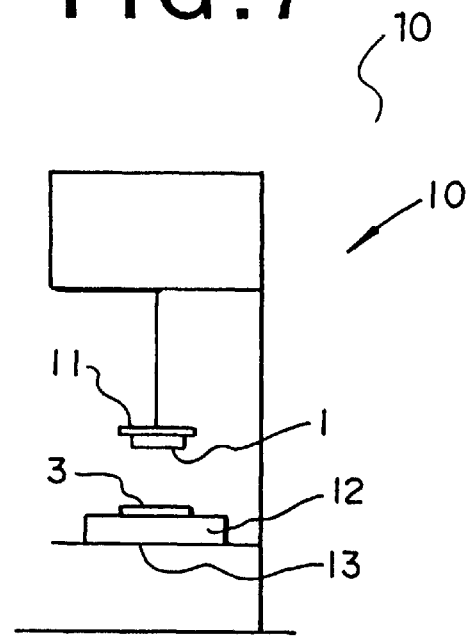
FIG. 7 is a diagrammatic illustration showing a machine which measures an adhesive force of the film preparation.
Figure 8:
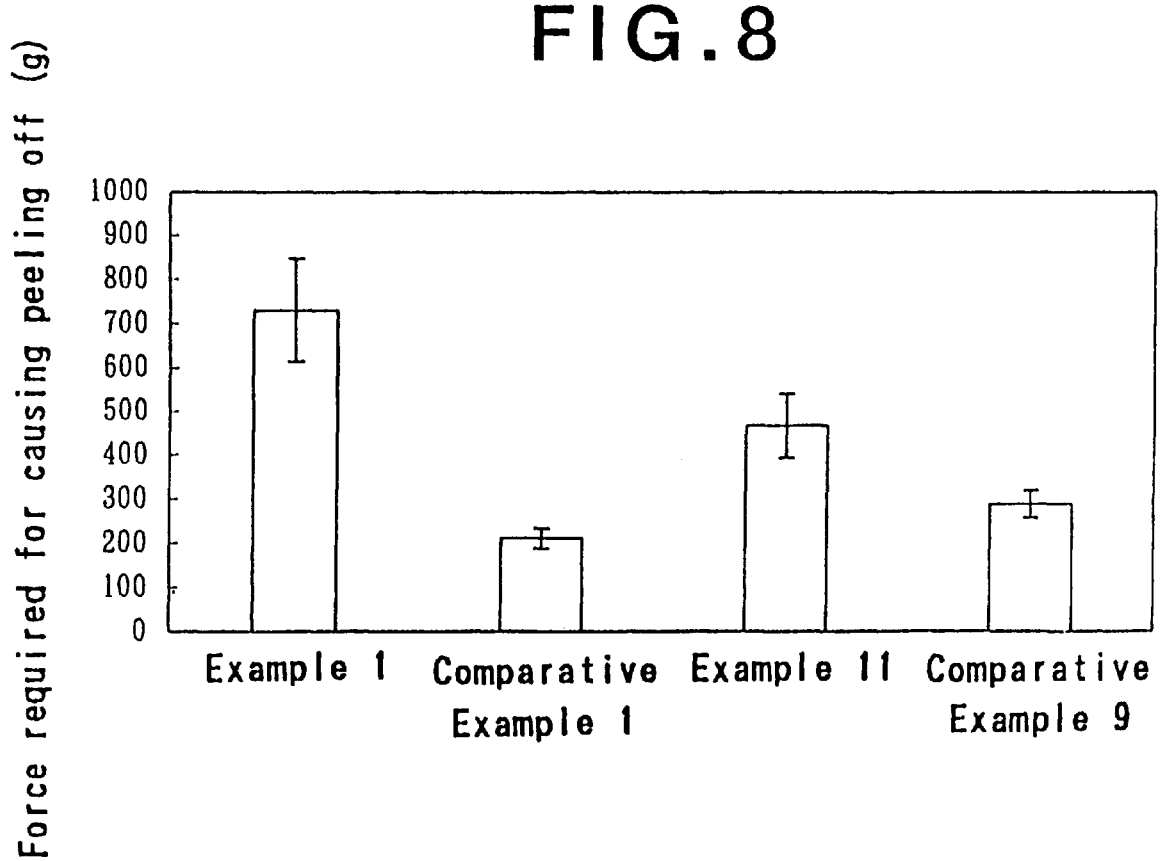
FIG. 8 is a graph showing results of a test for measuring the adhesive force of the preparation.
Figure 9:
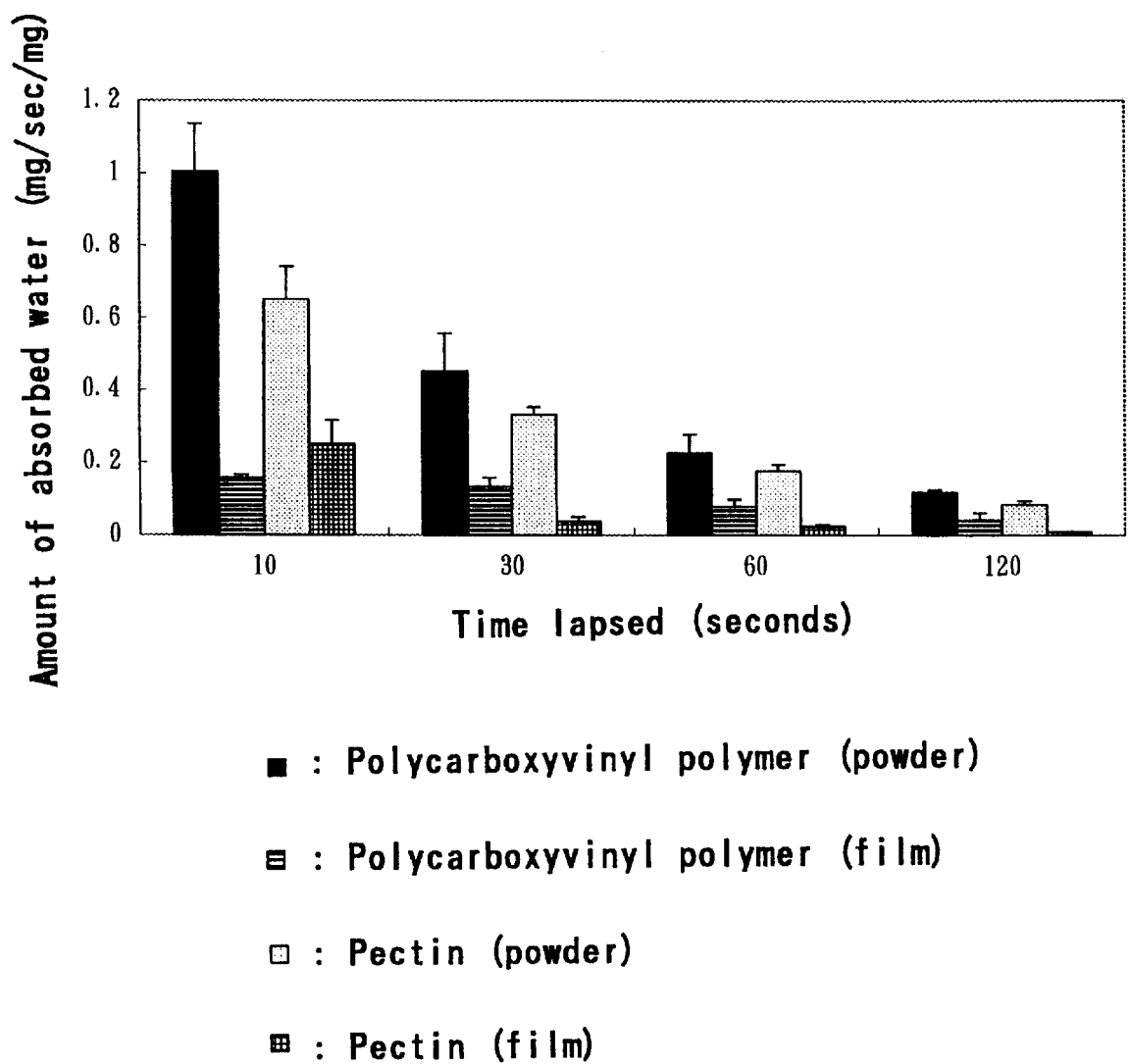
FIG. 9 is a graph showing results of a test for measuring an amount of adsorbed water.

A force of adhesion of the film preparation obtained by Examples 1 and 11 (with powdered adhesive high molecular weight substance) and a conventional film preparation obtained by Comparative Examples 1 and 9 (the adhesive high molecular weight substance is dissolved and dried to prepare a film-like state) was compared with use of a rheometer 10 as shown in FIG. 7.

Namely, non-adhesive surface of the preparation 1 was adhered to an adapter 11 of a disc having a diameter of 2 cm and the adapter was set to the rheometer 10. A bakelite plate 12 was placed on a sample table 13 and a carboxymethyl-cellulose (CMC) membrane 3 was placed thereon. Just after dropped water of 10 µl on the CMC membrane, the sample stand 13 was moved upwardly to press the preparation between the CMC membrane and adapter by a force of 1000 g for 60 seconds. Then, the sample plate was moved downwardly by 10 mm/min to cause a peeling off of the preparation from the sample table, so as to measure a force of adhesion of the preparation. The test was carried out by 3 times on each test preparation.

Results are shown in following Table 5. As apparently seen therefrom, the force of adhesion of the preparation according to the invention is higher than that of the conventional preparation with a significant difference.

TABLE 5

| | | Force of adhesion (g) | |
|---|---|---|---|
| Preparation | Adhesive substance | Average | Standard deviation |
| Example 1 | carboxyvinylpolymer | 729.7 | 115.7 |
| Com. Ex. 1 | carboxyvinylpolymer | 238.0 | 23.5 |
| Example 11 | pectin | 468.7 | 73.9 |
| Com. Ex. 9 | pectin | 290.0 | 30.8 |

In the Table,

Example: powder-applying method,

Comparative Example: solution-splaying method.

Test Example 6

(Test on absorption of water)

An absorptive power of water of an adhesive high molecular weight substance in powder state and film state was compared by a tea bag method and sheet methods which are simple methods on absorptive power of water regarding general high molecular weight substances and described in "Manufacture of functional polymer gel and its application", edited by Masahiro Irie, CMC Co. Ltd., 1987).

Firstly, a solution of carboxyvinyl polymer (190 mg) in ethanol (10 ml) was poured into a Φ 10 cm petori dish and gradually dried to obtain a film. Similarly, a pectin film was obtained by using the a pectin (190 mg) and water (20 ml).

On a tape with an adhesive layer on both surfaces which was adhered and carried on a polyvinyl chloride (PVC) film (thickness: 200 μm, surface area 2×2 $cm^2$), a powder of a high molecular weight substance (10 mg) or said film was applied and then the free surface of the PVC film was fixed on one end of a horizontal propeller, each of which wings has a length of 4 cm and width of 2 cm.

Thereafter, water of 1 ml was dropped on the powder layer or said film and left to stand for a constant period of time (10, 30, 60 and 120 seconds) and then the propeller was rotated for 10 seconds at 500 rpm to remove excess moisture. By measuring weight of the propeller to check weight of water absorbed by the powder or film of high molecular weight substance. The procedure was repeated by 3 times to calculate an amount of water (mg) per unit time (1 second) and unit weight (1 mg of the substance). For a compensation, similar procedure was carried out on the PVC film per se having no adhesive substance in the form of powder or film.

Results are shown in following Table 6. As apparently seen therefrom that an adsorption efficiency of carboxyvinyl polymer and pectin in the form of powder is higher with a significant difference than that in film state. Especially, an amount of absorbed water in case of the powder state and lapsing time of 10 seconds is remarkably high and this estimate that the preparation having the adhesive substance in the form of powder rapidly absorbs the moisture from an affected part and expands to develop an excellent force of adhesion.

TABLE 6

| Adhesive substance | Form | Time (sec) | Water absorption speed (mg/sec/mg) | |
|---|---|---|---|---|
| | | | Average | Standard deviation |
| Carboxyvinyl polymer | powder | 10 | 1.005 | 0.131 |
| | | 30 | 0.451 | 0.106 |
| | | 60 | 0.224 | 0.051 |
| | | 120 | 0.117 | 0.006 |
| Carboxyvinyl polymer | film | 10 | 0.157 | 0.008 |
| | | 30 | 0.132 | 0.024 |
| | | 60 | 0.078 | 0.019 |
| | | 120 | 0.042 | 0.017 |
| Pectin | powder | 10 | 0.651 | 0.094 |
| | | 30 | 0.329 | 0.023 |
| | | 60 | 0.175 | 0.018 |
| | | 120 | 0.083 | 0.011 |
| Pectin | film | 10 | 0.248 | 0.067 |
| | | 30 | 0.038 | 0.012 |
| | | 60 | 0.025 | 0.004 |
| | | 120 | 0.009 | 0.002 |

What is claimed is::

1. A multi-layered film preparation comprising:
    a drug-containing layer which contains a water-soluble high molecular weight compound as a main base material,
    a non-adhesive layer which is made difficult to dissolve in water and positioned on one surface of said drug-containing layer, and
    an adhesive compound positioned on the other surface of said drug-containing layer,
    wherein said adhesive compound in the final product is in the form of powder.

2. A multi-layered film preparation as claimed in claim 1, wherein said adhesive compound in the form of powder is forming an adhesive layer.

3. A multi-layered film preparation as claimed in claim 1, wherein said adhesive compound in the form of powder is carried on the drug-containing layer.

4. A multi-layered film preparation as claimed in claim 1, wherein said adhesive compound in the form of powder is dispersed in the drug-containing layer.

5. A multi-layered film preparation as claimed in claim 1, wherein said adhesive compound is at least one of materials selected from the group consisting of carboxyvinylpolymer, acrylic copolymer, non-toxic salt thereof, carboxymethylcellulose, salt thereof, pullulan, povidone, karaya gum, pectin, xanthane gum, tragacanth, arginic acid, gum arabic, acidic polysaccharide and its non-toxic salt.

6. A multi-layered film preparation as claimed in claim 1, wherein said drug-containing layer comprises at least one of drugs selected from the group consisting of a local anesthetic agent, analgesical-inflammatorical agent, steroid, hemostatic agent, fungicide, antiviral agent, antibiotic and synthetic antibacterial agent.

7. A multi-layered film preparation as claimed in claim 1, which is applied to cure erosion of mucous membrane in oral cavity, due to a side effect of a radiotherapy and chemotherapy as well as an infectious disease.

8. A multi-layered film preparation as claimed in claim 1, wherein said water-soluble high molecular weight compound is at least one of materials selected from the group consisting of hydroxypropylcellulose, hydroxypropylmethylcellulose, methylcellulose, carboxymethylcellulose, and a salt thereof, polyvinylalcohol and polyethylene oxide.

9. A multi-layered film preparation as claimed in claim 1, wherein said non-adhesive layer made difficult to dissolve in water contains at least one of materials selected from the group consisting of shellac, higher fatty acid, cellulose derivative having low solubility to water and enteric film forming agent.

10. A multi-layered film preparation consisting essentially of:
    a drug-containing layer which contains a water-soluble high molecular weight compound as a main base material,
    a non-adhesive layer which is made difficult to dissolve in water and positioned on one surface of said drug-containing layer, and
    an adhesive compound positioned on the other surface of said drug containing layer,
    wherein said adhesive compound in the final product is in the form of powder.

11. A multi-layered film preparation as claimed in claim 10, wherein said water-soluble high molecular weight compound is at least one of materials selected from the group consisting of hydroxypropylcellulose, hydroxypropylmethylcellulose, methylcellulose, carboxymethylcellulose, and a salt thereof, polyvinylalcohol and polyethylene oxide.

12. In a multi-layered film preparation comprising a drug-containing layer which contains a water-soluble high molecular weight compound as a main base material, a non-adhesive layer which is made difficult to dissolve in water and positioned on one surface of said drug-containing layer, and an adhesive compound positioned on the other surface of said drug-containing layer, the improvement comprising providing the adhesive compound in the final product in the form of powder.

13. A multi-layered film preparation as claimed in claim 12, wherein said water-soluble high molecular weight compound is at least one of materials selected from the group-consisting of hydroxypropylcellulose, hydroxypropylmethylcellulose, methylcellulose, carboxymethylcellulose, and a salt thereof, polyvinylalcohol and polyethylene oxide.

* * * * *

UNITED STATES PATENT AND TRADEMARK OFFICE
CERTIFICATE OF CORRECTION

PATENT NO.  :  5,914,118

DATED       :  June 22, 1999

INVENTOR(S) :  Yamamura et al.

It is certified that error appears in the above-identified patent and that said Letters Patent is hereby corrected as shown below:

```
On the title page, item [54] and column 1;
   Delete            ( MULTI-LAYERED DRUG CONTAINING FILM PREPARATION HAVING POWDER ADHESIVE THEREON ),  -- Insert --

" MULTI-LAYERED DRUG FILM PREPARATION HAVING POWER ADHESIVE

THEREON "
```

Signed and Sealed this

Fourteenth Day of December, 1999

Attest:

Q. TODD DICKINSON

*Attesting Officer*   *Acting Commissioner of Patents and Trademarks*